United States Patent [19]
Lambert et al.

[11] Patent Number: 5,721,193
[45] Date of Patent: Feb. 24, 1998

[54] 2-OXIMINOMETHYL-1-PHENYL-1,3-PROPANEDIONE DERIVATIVES AS HERBICIDES

[75] Inventors: Claude Lambert, Ibaraki, Japan; John Morris, Essex, England

[73] Assignee: Rhone-Poulenc Agriculture Limited, Ongar, England

[21] Appl. No.: 596,130

[22] PCT Filed: Aug. 4, 1994

[86] PCT No.: PCT/EP94/02580

§ 371 Date: Apr. 4, 1996

§ 102(e) Date: Apr. 4, 1996

[87] PCT Pub. No.: WO95/04716

PCT Pub. Date: Feb. 16, 1995

[30] Foreign Application Priority Data

Aug. 11, 1993 [GB] United Kingdom ............... 93 16689

[51] Int. Cl.$^6$ ............... A01N 35/10; C07C 249/08; C07C 251/34; C07C 291/62
[52] U.S. Cl. ............................ 504/344; 564/256
[58] Field of Search ............... 564/256; 504/344

[56] References Cited

U.S. PATENT DOCUMENTS 4,647,698  3/1987  Henrick .................. 564/256

FOREIGN PATENT DOCUMENTS

| 0 004 754 | 10/1979 | European Pat. Off. . |
| 0 024 888 | 3/1981 | European Pat. Off. . |
| 0 418 175 | 3/1991 | European Pat. Off. . |
| 0 487 357 | 5/1992 | European Pat. Off. . |
| 0 524 018 | 1/1993 | European Pat. Off. . |
| 0 527 036 | 2/1993 | European Pat. Off. . |
| 0 527 037 | 2/1993 | European Pat. Off. . |
| 2225014 | 5/1990 | United Kingdom . |

*Primary Examiner*—José G. Dees
*Assistant Examiner*—Barbara Badio
*Attorney, Agent, or Firm*—Burns, Doane, Swecker & Mathis, L.L.P.

[57] ABSTRACT

The invention relates to oxime derivatives of formula (I)

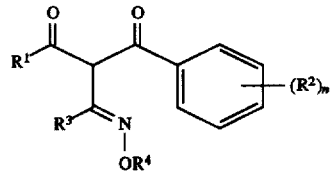

wherein $R^1$, $R^2$, $R^3$ $R^4$ and n are as defined in the specification. The invention is directed to compounds and agriculturally acceptable salts or metal complexes thereof, herbicidal compositions and a process for the preparation of the instant compounds.

16 Claims, No Drawings

2-OXIMINOMETHYL-1-PHENYL-1,3-PROPANEDIONE DERIVATIVES AS HERBICIDES

This Appln is a 371 of PCT/EP94/02580 Aug. 4, 1994.

FIELD OF THE INVENTION

This invention relates to novel oxime derivatives, compositions containing them, processes for their preparation, intermediates in their synthesis, and their use as herbicides.

BACKGROUND ART

In European Patent Publication Nos. 04754 and 024888 there are disclosed, as insecticides, ketoximinoethers of general structure Ar(R)C=NO—Q, where Ar may be optionally substituted phenyl, R is optionally substituted alkyl, cycloalkyl or alkenyl, and Q is optionally substituted 2-furyl-CHD—, 2-thienyl-CHD— or phenyl-CHD—, where D is hydrogen, cyano, thiocarboxamido, alkyl or ethynyl.

DESCRIPTION OF THE INVENTION

The present invention provides novel oxime derivatives of formula I:

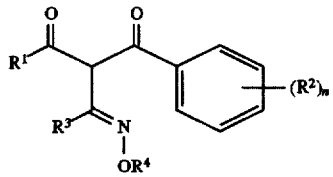

wherein:

$R^1$ represents:

a straight- or branched-chain alkyl group containing up to six carbon atoms which is optionally substituted by one or more halogen atoms; or a cycloalkyl group containing from three to six carbon atoms optionally substituted by one or more groups which may be the same or different selected from $R^5$, halogen, —$CO_2R^6$, —$SR^{51}$ and —$OR^6$;

$R^2$ represents:

a straight- or branched-chain alkyl, alkenyl or alkynyl group containing up to six carbon atoms optionally substituted by one or more halogen atoms;

a straight- or branched-chain alkyl group containing up to six carbon atoms which is substituted by a group —$OR^6$;

a group selected from halogen, nitro, cyano, —$CO_2R^6$, —$COR^6$, —X—$S(O)_qR^{51}$, —$S(O)_pR^{51}$, —$O(CH_2)_mOR^6$, —$NR^7R^8$, —$CONR^7R^8$ and —$OR^6$;

phenyl optionally substituted by from one to five groups $R^{21}$ which may be the same or different; or a cycloalkyl group containing from three to six carbon atoms optionally substituted by one or more groups which may be the same or different selected from $R^5$, halogen, —$CO_2R^6$, —$SR^{51}$ and —$OR^6$;

$R^3$ represents:

the hydrogen atom;

a straight- or branched-chain alkyl group containing up to six carbon atoms optionally substituted by one or more halogen atoms;

a cycloalkyl group containing from three to six carbon atoms optionally substituted by one or more groups $R^5$ or one or more halogen atoms which may be the same or different; or phenyl optionally substituted by from one to five groups $R^{21}$ which may be the same or different;

$R^4$ represents:

a straight- or branched-chain alkyl, alkenyl or alkynyl group containing up to six carbon atoms optionally substituted by one or more groups which may be the same or different selected from halogen, —$OR^6$ and phenyl optionally substituted by up to five groups $R^{21}$ which may be the same or different;

a cycloalkyl group containing from three to six carbon atoms optionally substituted by one or more groups which may be the same or different selected from $R^5$, halogen, —$CO_2R^6$, —$SR^{51}$ and —$OR^6$;

or phenyl optionally substituted by up to five groups $R^{21}$ which may be the same or different;

n represents zero or an integer from one to five;

$R^5$ and $R^6$, which may be the same or different, each represents a straight- or branched-chain alkyl group containing up to six carbon atoms which is optionally substituted by one or more halogen atoms;

$R^{51}$ represents a straight- or branched-chain alkyl group containing up to six carbon atoms which is optionally substituted by one or more halogen atoms;

X represents oxygen, —$(CR^9R^{10})_t$— or —$N(R^{11})$—;

p represents zero, one or two; q represents zero, one or two;

m represents an integer from one to three;

$R^7$ and $R^8$, which may be the same or different, each represents:

the hydrogen atom; or a straight- or branched-chain alkyl group containing up to six carbon atoms optionally substituted by one or more halogen atoms;

$R^9$ and $R^{10}$, which may be the same or different, each represents:

the hydrogen atom;

a straight- or branched-chain alkyl or alkenyl group containing up to six carbon atoms which is optionally substituted by one or more halogen atoms; or phenyl optionally substituted by from one to five groups $R^{21}$ which may be the same or different;

t represents an integer from one to four; when t is greater than one the groups —$CR^9R^{10}$— may be the same or different;

$R^{11}$ represents:

the hydrogen atom;

a straight- or branched-chain alkyl, alkenyl or alkynyl group containing up to ten carbon atoms which is optionally substituted by one or more halogen atoms; or phenyl optionally substituted from one to five groups $R^{21}$ which may be the same or different;

$R^{21}$ represents halogen, $R^6$, —$CO_2R^6$, —$COR^6$, —$OR^6$, nitro or cyano;

and agriculturally acceptable salts or metal complexes thereof, which possess valuable herbicidal properties.

It will be understood that the compounds of formula I may exist in enolic tautomeric forms that may give rise to geometric isomers around the enolic double bond. Furthermore, in certain cases the groups $R^1$, $R^2$, $R^3$, $R^4$, $R^5$, $R^6$, $R^7$, $R^8$, $R^9$, $R^{10}$, $R^{11}$, $R^{21}$ and $R^{51}$ may give rise to stereoisomers and geometric isomers. All such forms are embraced by the present invention.

By the term "agriculturally acceptable salts" is meant salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts.

Suitable acid addition salts, formed by compounds of formula I containing an amino group, include salts with inorganic acids, for example hydrochlorides, sulphates, phosphates and nitrates and salts with organic acids, for example acetic acid.

By the term "metal complexes" is meant compounds in which one or both of the oxygen atoms of the 1,3-dione, or the nitrogen atom of the oxime group act as chelating agents to a metal cation. Examples of such cations include zinc, manganese, cupric, cuprous, ferric, ferrous, titanium and aluminium.

DETAILED DESCRIPTION OF THE INVENTION

Preferably $R^1$ represents:

a straight- or branched-chain alkyl group containing up to six carbon atoms which is optionally substituted by one or more halogen atoms; or a cycloalkyl group containing from three to six carbon atoms optionally substituted by one or more methyl groups.

More preferably $R^1$ represents a group selected from methyl, ethyl, isopropyl, 1-methylcyclopropyl and, most preferably, cyclopropyl.

Compounds of formula I in which the phenyl ring is 2,4-disubstituted by two groups $R^2$; or is 2,3,4-trisubstituted by three groups $R^2$ are also preferred.

Preferably $R^2$ represents:

a halogen atom;

a straight- or branched-chain alkyl, alkenyl or alkynyl group containing up to four carbon atoms optionally substituted by one or more halogen atoms;

a straight- or branched-chain alkyl group containing up to four carbon atoms which is substituted by a group —$OR^6$; or a group selected from —$COR^6$, —$CO_2R^6$, —$S(O)_pR^{51}$, —$X$—$S(O)_qR^{51}$, —$O(CH_2)_mOR^6$ and —$OR^6$;

wherein X represents —$CH_2$— or —$NR^{11}$—; $R^6$ represents a straight- or branched-chain alkyl group containing up to four carbon atoms; and $R^{51}$ represents a straight- or branched-chain alkyl group containing up to four carbon atoms.

More preferably $R^2$ represents:

a halogen atom;

a straight- or branched-chain alkyl group containing up to four carbon atoms optionally substituted by one or more halogen atoms;

a straight- or branched-chain alkyl group containing up to four carbon atoms which is substituted by a group —$OR^6$; or a group —$S(O)_pR^{51}$, wherein $R^{51}$ represents ethyl or most preferably methyl.

Preferably $R^3$ represents the hydrogen atom or a straight- or branched-chain alkyl group containing up to four carbon atoms.

In a preferred embodiment $R^4$ represents a straight- or branched-chain alkyl or alkenyl group containing up to six carbon atoms (e.g. ethyl or 2-propenyl).

Preferably $R^{11}$ represents the hydrogen atom or a straight- or branched-chain alkyl group containing up to six carbon atoms.

Preferably n represents one, two or three, most preferably two or three.

A further preferred class of compounds of formula I are those in which:

$R^1$ represents a cyclopropyl group;

$R^2$ represents a halogen atom or a group selected from trifluoromethyl, —$S(O)_pR^{51}$ and —$X$—$S(O)_qR^{51}$;

$R^3$ represents the hydrogen atom;

$R^4$ represents a straight- or branched-chain alkyl or alkenyl group containing from two to four carbon atoms;

n represents two or three;

$R^{51}$ represents methyl;

X represents —$CH_2$—;

p represents zero, one or two; and q represents zero, one or two.

The following compounds of formula I are of particular interest:

1. 3-cyclopropyl-2-(ethoxyiminomethyl)-1-(2-methylsulphonyl-4-trifluoromethylphenyl)propan-1,3-dione; RPA203038

2. 3-cyclopropyl-1-(2-methylsulphonyl-4-trifluoromethylphenyl)-2-(2-propenyloxyiminomethyl)propan-1,3-dione; RPA203039

3. 1-(4-chloro-2-methylsulphonylphenyl)-3-cyclopropyl-2-(ethoxyiminomethyl)propan-1,3-dione; RPA203154

4. 1-(2-chloro-4-methylsulphonylphenyl)-3-cyclopropyl-2-(ethoxyiminomethyl)propan-1,3-dione; RPA203253

5. 1-(4-chloro-3-fluoro-2-methylsulphenylphenyl)-3-cyclopropyl-2-(ethoxyiminomethyl)propan-1,3-dione; RPA204081

6. 3-cyclopropyl-1-(3,4-dichloro-2-methylsulphenylphenyl)-2-(ethoxyiminomethyl)propan-1,3-dione; RPA204082

7. 1-[4-bromo-2-(methylsulphenylmethyl)phenyl]-3-cyclopropyl-2-(ethoxyiminomethyl)propan-1,3-dione; RPA204904

8. 1-[4-bromo-2-(methylsulphinylmethyl)phenyl]-3-cyclopropyl-2-(ethoxyiminomethyl)propan-1,3-dione; RPA204905 and 9. 1-[4-bromo-2-(methylsulphonylmethyl)phenyl]-3-cyclopropyl-2-(ethoxyiminomethyl)propan-1,3-dione. RPA204906

The following compounds of formula I in the table below also form part of the invention. Note that in the table and description that follows Cpd. means compound; cPr means cyclopropyl; iPr means isopropyl; Et means ethyl; Me means methyl; Bu means n-butyl; Pr means propyl; etc. Also, in the table, subscripts have not been used, but are understood (e.g. 2-SO2Me-4-CF3 means 2-$SO_2$Me-4-$CF_3$; CH2CH=CH2 means —$CH_2$CH=$CH_2$; 4-Cl-2-SO2Me means 2-chloro-4-$SO_2$Me; 3,4-Cl2-2-SMe means 3,4-dichloro-2-SMe, etc).

| Cpd. | $R^1$ | $(R^2)_n$ | $R^3$ | $R^4$ |
|---|---|---|---|---|
| 1 | cPr | 2-SO2Me-4-CF3 | H | Et |
| 2 | cPr | 2-SO2Me-4-CF3 | H | CH2CH=CH2 |
| 3 | cPr | 4-Cl-2-SO2Me | H | Et |
| 4 | cPr | 2-Cl-4-SO2Me | H | Et |
| 5 | cPr | 4-Cl-3-F-2-SMe | H | Et |
| 6 | cPr | 3,4-Cl2-2-SMe | H | Et |
| 7 | cPr | 2-CH2SMe-4-Br | H | Et |
| 8 | cPr | 2-CH2SOMe-4-Br | H | Et |
| 9 | cPr | 2-CH2SO2Me-4-Br | H | Et |
| 10 | cPr | 2-SO2Me-4-CF3 | H | Me |
| 11 | cPr | 2-NMeSO2Me-4-CF3 | Pr | CH2CH=CH2 |
| 12 | cPr | 3,4-Cl2-2-SMe | Pr | CH2CH=CH2 |
| 13 | cPr | 2-SMe-4-CF3 | Et | Et |

| Cpd. | R¹ | (R²)ₙ | R³ | R⁴ |
|---|---|---|---|---|
| 14 | cPr | 2-SO2Me-4-CF3 | Me | Hexyl |
| 15 | cPr | 2-SMe-4-CF3 | H | Me |
| 16 | cPr | 2-SO2Me-4-CF3 | Me | Me |
| 17 | cPr | 2-SMe-3,4-F2 | H | Me |
| 18 | cPr | 2-SO2Me-3,4-F2 | H | Me |
| 19 | cPr | 4-Cl-3-F-2-SMe | H | Me |
| 20 | cPr | 2-SMe-3-OMe-4-Cl | Et | Et |
| 21 | cPr | 2-CH2SOMe-4-Br | H | Bu |
| 22 | cPr | 2-NMeSO2Me-4-Cl | H | Me |
| 23 | cPr | 2-SMe-4-CF3 | H | Pr |
| 24 | cPr | 2-SO2Me-4-CF3 | Me | iPr |
| 25 | cPr | 2-Me-4-SMe | Et | Et |
| 26 | cPr | 2-SMe-3-OMe-4-Cl | H | Me |
| 27 | cPr | 2-CH2SO2Me-4-Br | H | Pr |
| 28 | cPr | 4-Cl-2-SO2Me | H | iPr |
| 29 | cPr | 2-SO2Me-3,4-F2 | H | Pr |
| 30 | cPr | 2-CH2SMe | H | Me |
| 31 | cPr | 2-NO2-4-Br | Et | Et |
| 32 | cPr | 2-Cl-4-SO2Me | H | iPr |
| 33 | cPr | 2-SO2Me-3,4-F2 | H | iPr |
| 34 | cPr | 2-Cl-4-SO2Me | H | Pr |
| 35 | cPr | 4-Cl-3-F-2-SMe | H | Pr |
| 36 | cPr | 2-SO2Me-3,4-F2 | H | Pr |
| 37 | cPr | 2-NMeSO2Me-4-CF3 | H | Et |
| 38 | cPr | 2-Cl-4-SO2Me | Pr | CH2CH=CH2 |
| 39 | cPr | 2-SO2Me-4-CF3 | H | Pr |
| 40 | cPr | 3,4-Cl2-2-SMe | H | iPr |
| 41 | cPr | 2-Cl-4-SO2Me | Et | Et |
| 42 | cPr | 2-CH2SMe | H | Et |
| 43 | cPr | 2-CH2SMe-4-Br | H | Pr |
| 44 | cPr | 2-NMeSO2Me-4-Cl | H | iPr |
| 45 | cPr | 2-SO2Me-4-CF3 | Me | CH2CH=CH2 |
| 46 | cPr | 2-CH2SO2Me-4-Br | H | Me |
| 47 | cPr | 2-NMeSO2Me-4-Cl | Pr | CH2CH=CH2 |
| 48 | cPr | 2-CH2SO2Me-4-Br | H | iPr |
| 49 | cPr | 2-CH2SMe | H | Bu |
| 50 | cPr | 2-CH2SOMe-4-Br | H | Me |
| 51 | cPr | 2-NMeSO2Me-4-CF3 | H | Pr |
| 52 | cPr | 2-CH2SOMe-4-Br | H | iPr |
| 53 | cPr | 2-SMe-4-CF3 | H | Bu |
| 54 | cPr | 4-Cl-2-SO2Me | H | Me |
| 55 | cPr | 2-NMeSO2Me-4-Cl | H | Et |
| 56 | cPr | 2-SMe-3-OMe-4-Cl | H | Et |
| 57 | cPr | 2-CH2SMe | H | Pr |
| 58 | cPr | 2-NMeSO2Me-4-Cl | H | Bu |
| 59 | cPr | 4-Cl-3-F-2-SMe | H | iPr |
| 60 | cPr | 2-SMe-3,4-F2 | H | iPr |
| 61 | cPr | 2-CH2SOMe-4-Br | H | Pr |
| 62 | cPr | 2-NMeSO2Me-4-CF3 | H | iPr |
| 63 | cPr | 4-Cl-2-SO2Me | H | Pr |
| 64 | cPr | 2-SO2Me-4-CF3 | H | Bu |
| 65 | cPr | 2-CH2SMe | Pr | CH2CH=CH2 |
| 66 | cPr | 2-SMe-3-OMe-4-Cl | H | Pr |
| 67 | cPr | 2-SMe-3-OMe-4-Cl | H | iPr |
| 68 | cPr | 2-SO2Me-3,4-F2 | H | Bu |
| 69 | cPr | 2-SMe-3,4-F2 | H | Bu |
| 70 | cPr | 3,4-Cl2-2-SMe | H | Pr |
| 71 | cPr | 2-SO2Me-4-CF3 | Me | Bu |
| 72 | cPr | 2-CH2SMe | H | iPr |
| 73 | cPr | 2-SO2Me-4-CF3 | H | Pentyl |
| 78 | cPr | 2-SMe-3,4-F2 | H | Bu |
| 75 | cPr | 2-SMe-3,4-F2 | H | Et |
| 80 | cPr | 2-SO2Me-3,4-F2 | H | Et |
| 77 | cPr | 2-SMe-3,4-F2 | H | iPr |
| 74 | cPr | 2-CH2SMe-4-Br | H | iPr |
| 79 | cPr | 2-Cl-4-SO2Me | H | Bu |
| 76 | cPr | 2-SMe-3,4-F2 | H | Pr |
| 81 | cPr | 2-CH2SO2Me-4-Br | H | Bu |
| 82 | cPr | 2-SO2Me-3,4-F2 | H | iPr |
| 83 | cPr | 2-SO2Me-4-CF3 | Me | Pr |
| 84 | cPr | 2-SMe-3,4-F2 | H | Me |
| 85 | cPr | 4-Cl-2-SO2Me | Pr | CH2CH=CH2 |
| 86 | cPr | 2-SMe-3,4-F2 | H | Pr |
| 87 | cPr | 3,4-Cl2-2-SMe | H | Bu |
| 88 | cPr | 2-CH2SMe-4-Br | H | Me |
| 89 | cPr | 2-SO2Me-3,4-F2 | H | Me |
| 90 | cPr | 2-SMe-3,4-F2 | Pr | CH2CH=CH2 |
| 91 | cPr | 4-Cl-3-F-2-SMe | H | Bu |
| 92 | cPr | 3,4-Cl2-2-SMe | H | Me |
| 93 | cPr | 4-Cl-2-SO2Me | H | Bu |
| 94 | cPr | 2-Cl-4-SO2Me | H | Me |
| 95 | cPr | 4-Cl-3-F-2-SMe | Et | Et |
| 96 | cPr | 2-SMe-3,4-F2 | Et | Et |
| 97 | cPr | 2-SO2Me-3,4-F2 | Et | Et |
| 98 | cPr | 2-CH2SMe | Et | Et |
| 99 | cPr | 2-NMeSO2Me-4-CF3 | Et | Et |
| 100 | cPr | 2-SO2Me-4-CF3 | Et | Et |
| 101 | cPr | 4-Cl-2-SO2Me | Et | Et |
| 102 | cPr | 2-CH2SOMe-4-Br | Et | Et |
| 103 | cPr | 2-NMeSO2Me-4-Cl | Et | Et |
| 104 | cPr | 3,4-Cl2-2-SMe | Et | Et |
| 105 | cPr | 2-Cl-4-SO2Me | Pr | Et |
| 106 | cPr | 4-Cl-3-F-2-SMe | Pr | Et |
| 107 | cPr | 2-SMe-3,4-F2 | Pr | Et |
| 108 | cPr | 2-SO2Me-3,4-F2 | Pr | Et |
| 109 | cPr | 2-CH2SMe | Pr | Et |
| 110 | cPr | 2-NMeSO2Me-4-CF3 | Pr | Et |
| 111 | cPr | 2-SO2Me-4-CF3 | Pr | Et |
| 112 | cPr | 4-Cl-2-SO2Me | Pr | Et |
| 113 | cPr | 2-CH2SOMe-4-Br | Pr | Et |
| 114 | cPr | 2-NMeSO2Me-4-Cl | Pr | Et |
| 115 | cPr | 3,4-Cl2-2-SMe | Pr | Et |
| 116 | iPr | 2-Cl-4-SO2Me | Pr | Et |
| 117 | iPr | 4-Cl-3-F-2-SMe | Pr | Et |
| 118 | iPr | 2-SMe-3,4-F2 | Pr | Et |
| 119 | iPr | 2-SO2Me-3,4-F2 | Pr | Et |
| 120 | iPr | 2-CH2SMe | Pr | Et |
| 121 | iPr | 2-NMeSO2Me-4-CF3 | Pr | Et |
| 122 | iPr | 2-SO2Me-4-CF3 | Pr | Et |
| 123 | iPr | 4-Cl-2-SO2Me | Pr | Et |
| 124 | iPr | 2-CH2SOMe-4-Br | Pr | Et |
| 125 | iPr | 2-NMeSO2Me-4-Cl | Pr | Et |
| 126 | iPr | 3,4-Cl2-2-SMe | Pr | Et |
| 127 | Me | 2-Cl-4-SO2Me | Pr | Et |
| 128 | Me | 4-Cl-3-F-2-SMe | Pr | Et |
| 129 | Me | 2-SMe-3,4-F2 | Pr | Et |
| 130 | Me | 2-SO2Me-3,4-F2 | Pr | Et |
| 131 | Me | 2-CH2SMe | Pr | Et |
| 132 | Me | 2-NMeSO2Me-4-CF3 | Pr | Et |
| 133 | Me | 2-SO2Me-4-CF3 | Pr | Et |
| 134 | Me | 4-Cl-2-SO2Me | Pr | Et |
| 135 | Me | 2-CH2SOMe-4-Br | Pr | Et |
| 136 | Me | 2-NMeSO2Me-4-Cl | Pr | Et |
| 137 | Me | 3,4-Cl2-2-SMe | Pr | Et |
| 138 | Bu | 2-Cl-4-SO2Me | Pr | Et |
| 139 | Bu | 4-Cl-3-F-2-SMe | Pr | Et |
| 140 | Bu | 2-SMe-3,4-F2 | Pr | Et |
| 141 | Bu | 2-SO2Me-3,4-F2 | Pr | Et |
| 142 | Bu | 2-CH2SMe | Pr | Et |
| 143 | Bu | 2-NMeSO2Me-4-CF3 | Pr | Et |
| 144 | Bu | 2-SO2Me-4-CF3 | Pr | Et |
| 145 | Bu | 4-Cl-2-SO2Me | Pr | Et |
| 146 | Bu | 2-CH2SOMe-4-Br | Pr | Et |
| 147 | Bu | 2-NMeSO2Me-4-Cl | Pr | Et |
| 148 | Bu | 3,4-Cl2-2-SMe | Pr | Et |
| 149 | cPr | 2-SO2Me-4-CF3 | H | Hexyl |
| 150 | cPr | 4-Cl-3-F-2-SMe | Pr | CH2CH=CH2 |
| 151 | cPr | 2-SO2Me-3,4-F2 | H | Et |
| 152 | cPr | 2-SO2Me-3,4-F2 | Pr | CH2CH=CH2 |
| 153 | cPr | 2-NMeSO2Me-4-Cl | H | Pr |
| 154 | cPr | 2-CH2SMe-4-Br | H | Bu |
| 155 | cPr | 2-SO2Me-4-CF3 | Pr | CH2CH=CH2 |
| 156 | cPr | 2-SMe-3,4-F2 | H | Et |
| 157 | cPr | 2-CH2SOMe-4-Br | Pr | CH2CH=CH2 |
| 158 | cPr | 2-SO2Me-4-CF3 | H | iPr |
| 159 | cPr | 2-NMeSO2Me-4-CF3 | H | Me |
| 160 | cPr | 2-SO2Me-4-CF3 | Me | Pentyl |
| 161 | cPr | 2-SMe-4-Cl | Et | Et |
| 162 | cPr | 2-OMe-4-SMe | Et | Et |
| 163 | cPr | 2-SMe-3-OMe-4-Cl | H | Bu |
| 164 | cPr | 2-SMe-4-CF3 | H | iPr |
| 165 | cPr | 2-NMeSO2Me-4-CF3 | H | Bu |

The numbers 1 to 165 are assigned to these compounds for reference and identification hereafter.

Compounds of formula I may be prepared by the application or adaptation of known methods (i.e. methods heretofore used or described in the literature), for example as hereinafter described.

It is to be understood that in the descriptions that follow the sequences may be performed in different orders, and suitable protecting groups may be required to achieve the compounds sought.

According to a feature of the invention compounds of formula I may be prepared by the reaction of a compound of formula II:

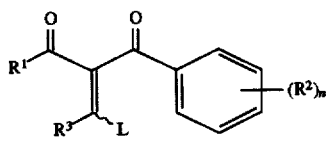

wherein $R^1$, $R^2$, $R^3$ and n are as hereinbefore defined and L is a leaving group, with the appropriate hydroxylamine of formula III:

   $R^4O-NH_2$   III or a salt thereof, wherein $R^4$ is as hereinbefore defined. Generally, L is alkoxy, e.g. ethoxy, or N,N-dialkylamino, e.g. N,N-dimethylamino. The reaction is generally carried out in an organic solvent such as ethanol, dichloromethane or acetonitrile, or a mixture of water-miscible organic solvent and water, in a ratio from 1:99 to 99:1, optionally in the presence of a base or acid acceptor such as triethylamine or sodium acetate, at a temperature from 0° C. to the boiling point of the solvent. Compounds of formula II in which $R^1$, $R^2$, m and L are as hereinbefore defined and $R^3$ is as hereinbefore defined excluding hydrogen, and their salts and metal complexes are novel and as such constitute a feature of the present invention.

Compounds of formula II in which L represents alkoxy may be prepared by the reaction of a compound of formula IV:

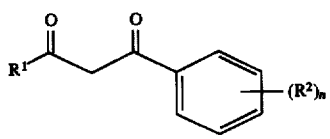

wherein $R^1$, $R^2$ and n are as hereinbefore defined, with a substituted trialkyl orthoformate (preferably, where $R^3$ is hydrogen, using triethyl orthoformate). Compounds of formula II in which L represents N,N-dialkylamino may be prepared by the reaction of a compound of formula IV above with a N,N-dimethylformamide dialkylacetal such as (where $R^3$ is hydrogen) N,N-dimethylformamide dimethyl acetal. The reaction with a trialkyl orthoformate is generally carried out in the presence of acetic anhydride at the reflux temperature of the mixture; and the reaction with a N,N-dimethyl formamide dialkyl acetal is carried out optionally in the presence of an inert solvent at a temperature from room temperature to the reflux temperature of the mixture.

Compounds of formula IV may be prepared by the reaction of an acid chloride of formula V:

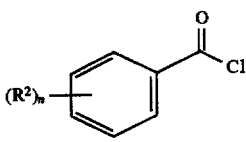

wherein $R^2$ and n are as hereinbefore defined, with the metal salt of a compound of formula VI:

$R^1COCH_2CO_2tBu$   VI wherein $R^1$ is as hereinbefore defined, to give a compound of formula VII:

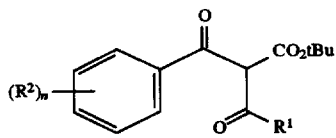

wherein $R^1$, $R^2$ and n are as hereinbefore defined, which is subsequently decarboxylated to give a compound of formula IV. Generally the reaction to produce the compound of formula VII is performed in a solvent such as a lower alcohol, preferably methanol, in the presence of a metal, preferably magnesium. The decarboxylation is generally performed by refluxing the compound of formula VII in the presence of a catalyst, such as paratoluenesulphonic acid or trifluoroacetic acid, in an inert solvent e.g. toluene or 1,2-dichloroethane.

Compounds of formula II in which $R^3$ represents hydrogen, and of formulae III, V and VI are known or can be prepared by known the application of known methods, see for example European Patent Publication Nos. 0418175, 0487357 and 0527036.

Compounds of formula I may be converted into agriculturally acceptable salts or metal complexes thereof by known methods or by the application and adaptation of known methods.

The following Examples illustrate the preparation of compounds of formula I and the following Reference Examples illustrate the preparation of intermediates of the invention. In the present specification b.p. means boiling point; m.p. means melting point. Where the letters NMR appear, there follow the characteristics of a proton nuclear magnetic spectrum.

EXAMPLE 1

A mixture of 3-cyclopropyl-2-ethoxymethylene-1-(2-methylsulphonyl-4-trifluoromethylphenyl)propan-1,3-dione (3.5 g), O-ethylhydroxylamine hydrochloride (0.97 g) and sodium acetate (0.83 g) in ethanol (15 ml) was stirred at 25° C. for 1 hour. The mixture was poured into water and extracted with ethyl acetate. The ethyl acetate solution was dried (anhydrous sodium sulphate) and filtered. The filtrate was evaporated and the residue purified by column chromatography on silica, using a mixture of ethyl acetate and hexane as eluent. The resulting solution was evaporated and 3-cyclopropyl-2-(ethoxyiminomethyl)-1-(2-methylsulphonyl-4-trifluoromethylphenyl)propan-1,3-dione (compound 1) was obtained as white crystals (2 g), m.p. 46° C.

By proceeding in a similar manner the following compounds were prepared from the appropriately substituted starting materials:

3-cyclopropyl-1-(2-methylsulphonyl-4-trifluoromethylphenyl)-2-(2-propenyloxyiminomethyl)

propan-1,3-dione (compound 2), NMR (CDCl$_3$) δ 1.0–1.3 (m, 4H), 2.6(m, 1H), 3.25(s, 3H), 4.3(m, 2H), 5.05(m, 1H), 5.3(m, 1H), 5.7(m, 1H), 7.5(m, 1H), 7.6(m, 1H), 7.9(m, 1H), 8.4(s, 1H), 17.4(s, 1H) ppm;

1-(4-chloro-2-methylsulphonylphenyl)-3-cyclopropyl-2-(ethoxyiminomethyl)propan-1,3-dione (compound 3), m.p. 115° C.;

1-(2-chloro-4-methylsulphonylphenyl)-3-cyclopropyl-2-(ethoxyiminomethyl)propan-1,3-dione (compound 4), m.p. 64° C.

1-[4-bromo-2-(methylsulphenylmethyl)phenyl]-3-cyclopropyl-2-(ethoxyiminomethyl)propan-1,3-dione (compound 7) as a brown oil, NMR (CDCl$_3$) δ 1.1–1.3(5H, m), 1.35(2H, m), 2.0(3H, s), 3.0(1H, m) 3.7(2H, s), 4.0–4.15 (2H, m), 7.1(1H, m), 7.45(1H, m), 7.6(2H, m), 17.65(1H, s).

EXAMPLE 2

A mixture of 1-(4-chloro-3-fluoro-2-methylsulphenylphenyl)-3-cyclopropyl-2-(dimethylaminomethylene)-propan-1,3-dione (3 g) and O-ethylhydroxylaminehydrochloride (1 g) in ethanol (20 ml) was stirred at 25° C. for 2 hours. The mixture was poured into water and extracted with dichloromethane. The solution was dried (anhydrous sodium sulphate) and filtered. The filtrate was evaporated and the mixture purified by column chromatography on silica, using a mixture of ethyl acetate and hexane as eluent. The resulting solution was evaporated and 1-(4-chloro-3-fluoro-2-methylsulphenylphenyl)-3-cyclopropyl-2-(ethoxyiminomethyl)-propan-1,3-dione (compound 5) was obtained as a reddish gum (2.4 -g), NMR (CDCl$_3$) δ 1.1–1.4 (m, 7H), 2.7(m, 1H), 2.4(s, 3H), 3.9(m, 2H), 7.0(m, 1H), 7.3(m, 1H), 7.6(s, 1H), 17.4(s, 1H) ppm.

By proceeding in a similar manner, 3-cyclopropyl-1-(3,4-dichloro-2-methylsulphenylphenyl)-2-(ethoxyiminomethyl)propan-1,3-dione (compound 6), NMR (CDCl$_3$) δ 1.1–1.4(m, 7H), 2.35(m, 1H), 2.4(s, 3H), 4.0(m, 2H), 7.1(m, 1H), 7.5(m, 1H), 7.6(s, 1H), 17.5(s, 1H) ppm, was prepared from the appropriately substituted starting materials.

EXAMPLE 3

To a stirred solution of 1-[4-bromo-2-(methylsulphenylmethyl)phenyl]-3-cyclopropyl-2-(ethoxyiminomethyl)propan-1,3-dione (0.95 g) in dichloromethane cooled to −25° C. was slowly added m-chloroperbenzoic acid (50 to 60%, 0.55 g). The mixture was filtered in the cold and the filtrate diluted with ether and washed with 1M sodium metabisulphite, 25% sodium acetate and brine, dried (anhydrous sodium sulphate) and evaporated. The residue was purified by column chromatography on silica gel, eluting with ethyl acetate and hexane, giving as a yellow gum 1-[4-bromo-2-(methylsulphinylmethyl)phenyl]-3-cyclopropyl-2-(ethoxyiminomethyl)propan-1,3-dione (compound 8, 0.78 g), NMR (CDCl$_3$) δ 1.0–1.4(7H, m), 2.55(3H, s), 2.8(1H, m), 4.0–4.2(4H, m), 7.2(1H, d), 7.5(1H, dd), 7.65(1H, d), 7.7(1H, bs).

EXAMPLE 4

A mixture of 1-[4-bromo-2-(methylsulphinylmethyl)phenyl]-3-cyclopropyl-2-(ethoxyiminomethyl)propan-1,3-dione (350 mg) and m-chloroperbenzoic acid (50–60%, 400 mg) in dichloromethane was stirred at room temperature for one hour. 1M sodium metabisulphite was added and the mixture cooled to 0° C. and filtered. The filtrate was diluted with ether, washed with 25% sodium acetate and brine, dried (anhydrous sodium sulphate) and evaporated. The residue was purified by column chromatography on silica gel, eluting with acetone and hexane, giving as a brown gum 1-[4-bromo-2-(methylsulphonylmethyl)phenyl]-3-cyclopropyl-2-(ethoxyiminomethyl)propan-1,3-dione (compound 9, 10 mg), NMR (CDCl$_3$) δ 1.0–1.2(7H, m), 2.45(1H, m), 2.8(3H, s), 4.05(2H, q), 4.6(2H, q), 7.5–7.6 (2H, m), 7.65–7.7(2H, m)

Reference Example 1

A mixture of 1-[4-bromo-2-(methylsulphenylmethyl)phenyl]-3-cyclopropylpropan-1,3-dione [4.4 g, containing approximately 1.0 g methyl 4-bromo-2-(methylsulphenylmethyl)benzoate], triethylorthoformate (3.5 ml) and acetic anhydride (2.9 ml) was heated at reflux for three hours. The mixture was then evaporated giving an impure sample of 1-[4-bromo-2-(methylsulphenylmethyl)phenyl]-3-cyclopropyl-2-ethoxymethylenepropane-1,3-dione as a red oil (4.8 g).

Reference Example 2

A mixture of t-butyl 2-(4-chloro-2-methylsulphonylbenzoyl)-3-cyclopropyl-3-oxopropionate (9.5 g) and 4-toluenesulphonic acid (1.5 g) in toluene was stirred and heated at reflux for 3 hours. After cooling, the mixture was washed with water, dried (anhydrous magnesium sulphate) and filtered. The filtrate was evaporated to dryness to give 1-(4-chloro-2-methylsulphonylphenyl)-3-cyclopropylpropan-1,3-dione, (7.1 g) as an orange gum, NMR (CDCl$_3$) δ 0.8–1.2(m, 4H), 1.5–1.9(m, 1H), 3.3(s, 3H), 5.8(s, 1H), 7.3–7.6(m, 2H), 7.9(s, 1H).

By proceeding in a similar manner the following compounds of formula IV above were prepared from the appropriately substituted starting materials:

| R$^1$ | (R$^2$)$_n$ | NMR (CDCl$_3$)/m.p. |
|---|---|---|
| cPr | 2-SO$_2$Me-4-CF$_3$ | NMR: 0.8–1.4(m, 4H), 1.5–1.8(m, 1H), 3.3(s, 3H), 5.85(s, 1H), 7.5(d, 1H), 7.8(d, 1H), 8.2(s, 1H) |
| cPr | 2-Cl-4-SO$_2$Me | 93.1° C. |
| cPr | 2-SMe-3-F-4-Cl | — |
| cPr | 2-SMe-3,4-diCl | 57–58.5° C. |

Reference Example 3

Carbon tetrachloride (2 ml) was added to a mixture of magnesium (0.57 g) and t-butyl 3-cyclopropyl-3-oxopropionate (4.36 g) in methanol. The mixture was stirred for 0.5 hours. It was evaporated to dryness and the residue was dissolved in toluene. The solution was evaporated to dryness and the residue was suspended in acetonitrile. 4-Chloro-2-methylsulphonylbenzoyl chloride (6.0 g) was added and the mixture was stirred for 3 hours. It was evaporated to dryness and the residue was dissolved in ethyl acetate. The mixture was washed with aqueous hydrochloric acid (2M), water, dried (anhydrous magnesium sulphate) and filtered. The filtrate was evaporated to dryness to give t-butyl 2-(4-chloro-2-methylsulphonylbenzoyl)-3-cyclopropyl-3-oxopropionate (9.6 g) as a brown oil which was not further purified.

By proceeding in a similar manner the following compounds of formula VII above were prepared from the appropriately substituted starting materials:

| R¹ | (R²)ₙ |
|---|---|
| cPr | 2-SO₂Me-4-CF₃ |
| cPr | 2-Cl-4-SO₂Me |
| cPr | 2-SMe-3-F-4-Cl |
| cPr | 2-SMe-3,4-diCl |

Benzoyl chlorides were prepared by heating the appropriately substituted benzoic acids at reflux with thionyl chloride for 3 hours. The excess thionyl chloride was removed by evaporation and the benzoyl chlorides thus obtained were used directly without further purification.

Benzoic acids are known, or may be prepared by the application of known methods, for example see European Patent Publication Nos. 0418175, 0487357 and 0527036.

Reference Example 4

A solution of cyclopropyl methyl ketone (1.1 g) and methyl 4-bromo-2-(methylsulphenylmethyl)benzoate (3.6 g) in tetrahydrofuran was added to a refluxing suspension of sodium hydride (80%, 0.9 g) in tetrahydrofuran. After the addition was complete, the mixture was maintained at reflux temperature for 30 minutes. It was then cooled and poured onto 100 g of ice and 50 ml of saturated aqueous sodium bicarbonate. The mixture was extracted with hexane, the organic solution dried (anhydrous sodium sulphate) and the solvent evaporated to give 1-[4-bromo-2-(methylsulphenylmethyl)phenyl]-3-cyclopropylpropan-1,3-dione as an orange oil (2.23 g), NMR (CDCl₃): 1.00(2H, m), 1.20(2H, m), 1.75(1H, m), 2.03(3H, s), 3.92(2H, s), 6.00 (1H, s), 7.35(1H, m), 7.45(1H, m), 7.58(1H, m) 14.74(1H, s).

Reference Example 5

A mixture of methyl 4-bromo-2-(bromomethyl)benzoate (12 g) and sodium thiomethoxide (2.5 g) in toluene was stirred at 100° C. for 2 hours. The mixture was then cooled, poured into water and extracted with ethyl acetate. The organic layer was separated, washed with brine, dried (anhydrous sodium sulphate) and evaporated to afford a brown oil which was purified by column chromatography on silica gel giving methyl 4-bromo-2-(methylsulphenylmethyl)benzoate (4.1 g) as white crystals, m.p. 79.3° C.

Reference Example 6

A mixture of methyl 4-bromo-2-methylbenzoate (45 g), N-bromosuccinimide (38.4 g) and dichloromethane was heated at reflux under irradiation from two 120 Watt tungsten lamps for five hours. The mixture was then cooled to −15° C. and filtered and the filtrate was evaporated. The residue was recrystallised from cyclohexane to give methyl 4-bromo-2-(bromomethyl)benzoate as pale yellow crystals (39.9 g), m.p. 79.2° C.

According to a feature of the present invention, there is provided a method for controlling the growth of weeds (i.e. undesired vegetation) at a locus which comprises applying to the locus a herbicidally effective amount of at least one oxime derivative of formula I or an agriculturally acceptable salts or metal complex thereof. For this purpose, the oxime derivatives are normally used in the form of herbicidal compositions (i.e. in association with compatible diluents or carriers and/or surface active agents suitable for use in herbicidal compositions), for example as hereinafter described.

The compounds of formula I show herbicidal activity against dicotyledonous (i.e. broad-leafed) and monocotyledonous (e.g. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutilon theophrasti*, *Amaranthus retroflexus*, *Bidens pilosa*, *Chenopodium album*, *Galium aparine*, *Ipomoea spp*. e.g. *Ipomoea purpurea*, *Sesbania exaltata*, *Sinapis arvensis*, *Solanum nigrum* and *Xanthium strumarium*, and grass weeds, for example *Alopecurus myosuroides*, *Arena fatua*, *Digitaria sanguinalis*, *Echinochloa crus-galli*, *Eleusine indica* and *Setaria spp*, e.g. *Setaria faberii* or *Setaria viridis*, and sedges, for example, *Cyperus esculentus*.

The amounts of compounds of formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula I may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula I may be incorporated into the soil in which the weeds are expected to emerge. It will be appreciated that when the compounds of formula I are used to control the growth of weeds by post-emergence application, i.e. by application to the aerial or exposed portions of emerged weeds, the compounds of formula I will also normally come into contact with the soil and may also then exercise a pre-emergence control on later-germinating weeds in the soil.

Where especially prolonged weed control is required, the application of the compounds of formula I may be repeated if required.

According to a further feature of the present invention, there are provided compositions suitable for herbicidal use comprising one or more of the oxime derivatives of formula I or an agriculturally acceptable salts or metal complex thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula I.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula I with solid diluents or by impregnating the solid diluents or carriers with solutions of the compounds of formula I in volatile solvents, evaporating the solvents and, if necessary, grinding the products so as to obtain powders. Granular formulations may be prepared by absorbing the compounds of formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula I may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of formula I, from 2 to 10% of surface-active agent, from 0.1 to 5% of thickener and from 15 to 87.9% of water;

wettable powders which comprise from 10 to 90% of one or more compounds of formula I, from 2 to 10% of surface-active agent and from 8 to 88% of solid diluent or carrier;

water soluble or water dispersible powders which comprise from 10 to 90% of one or more compounds of formula I, from 2 to 40% of sodium carbonate and from 0 to 88% of solid diluent;

liquid water soluble concentrates which comprise from 5 to 50%, e.g. 10 to 30%, of one or more compounds of formula I, from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula I, from 5 to 15% of surface-active agent, from 0.1 to 5% of thickener and from 10 to 84.9% of organic solvent;

granules which comprise from 1 to 90%, e.g. 2 to 10% of one or more compounds of formula I, from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula I, from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2-dimethyl-3,5-diphenylpyrazolium salts], flampropmethyl [methyl N-2-(N-benzoyl-3-chloro-4-fluoroanilino)-propionate], fluometuron [N'-(3-trifluoromethylphenyl)-N,N-dimethylurea], isoproturon [N'-(4-isopropylphenyl)-N,N-dimethylurea], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

The following Examples illustrate herbicidal compositions according to the present invention:

Example C1

| A soluble concentrate is formed from: | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 was obtained then making up to volume with water.

Similar soluble concentrates may be prepared as described above by replacing the oxime (compound 1) with other compounds of formula I.

Example C2

| A wettable powder is formed from: | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the oxime (compound 1) with other compounds of formula I.

Example C3

| A water soluble powder is formed from: | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the oxime (compound 1) with other compounds of formula I.

Representative compounds of formula I have been used in herbicidal applications according to the following procedures.

METHOD OF USE OF HERBICIDAL COMPOUNDS a) General

Appropriate quantities of the compounds used to treat the plants were dissolved in acetone to give solutions equivalent to application rates up to 4000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

|  | Approx number of seeds/pot |
|---|---|
| Weed species | |
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2. |
| 2) Grass weeds | |
| Alopecurus myosuroides | 15 |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

|  | Number of plants per pot | Growth stage |
|---|---|---|
| 1) Broad leafed weeds | | |
| Weed species | | |
| Abutilon theophrasti | 3 | 1–2 leaves |
| Amaranthus retroflexus | 4 | 1–2 leaves |
| Galium aparine | 3 | 1st whorl |
| Ipomoea purpurea | 3 | 1–2 leaves |
| Sinapis arvensis | 4 | 2 leaves |
| Xanthium strumarium | 1 | 2–3 leaves. |
| 2) Grass weeds | | |
| Weed species | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |
| 3) Sedges | | |
| Weed species | | |
| Cyperus esculentus | 3 | 3 leaves. |
| 1) Broad leafed | | |
| Crops | | |
| Cotton | 2 | 1 leaf |
| Soya | 2 | 2 leaves. |
| 2) Grass | | |
| Crops | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

When applied either pre- or post-emergence at 1 Kg/ha or less, compounds 1 to 9 gave at least 90% control of one or more weed species, together which selectivity in at least one crop species.

We claim:

1. An oxime derivative characterised by the formula I:

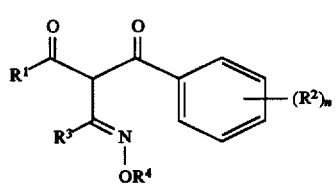

wherein:

$R^1$ represents:

a straight- or branched-chain alkyl group containing up to six carbon atoms which is optionally substituted by one or more halogen atoms; or a cycloalkyl group containing from three to six carbon atoms optionally substituted by one or more groups which may be the same or different selected from $R^5$, halogen, $-CO_2R^6$, $-SR^{51}$ and $-OR^6$;

$R^2$ represents:

a straight- or branched-chain alkyl, alkenyl or alkynyl group containing up to six carbon atoms optionally substituted by one or more halogen atoms;

a straight- or branched-chain alkyl group containing up to six carbon atoms which is substituted by a group $-OR^6$;

a group selected from halogen, nitro, cyano, $-CO_2R^6$, $-COR^6$, $-X-S(O)_pR^{51}$, $-S(O)_pR^{51}$, $-O(CH_2)_mOR^6$, $-NR^7R^8$, $-CONR^7R^8$ and $-OR^6$;

phenyl optionally substituted by from one to five groups $R^{21}$ which may be the same or different; or a cycloalkyl group containing from three to six carbon atoms optionally substituted by one or more groups which may be the same or different selected from $R^5$, halogen, $-CO_2R^6$, $-SR^{51}$ and $-OR^6$;

$R^3$ represents:

the hydrogen atom;

a straight- or branched-chain alkyl group containing up to six carbon atoms optionally substituted by one or more halogen atoms;

a cycloalkyl group containing from three to six carbon atoms optionally substituted by one or more groups $R^5$ or one or more halogen atoms which may be the same or different; or phenyl optionally substituted by from one to five groups $R^{21}$ which may be the same or different;

$R^4$ represents:

a straight- or branched-chain alkyl, alkenyl or alkynyl group containing up to six carbon atoms optionally substituted by one or more groups which may be the same or different selected from halogen, $-OR^6$ and phenyl optionally substituted by up to five groups $R^{21}$ which may be the same or different;

a cycloalkyl group containing from three to six carbon atoms optionally substituted by one or more groups which may be the same or different selected from $R^5$, halogen, $-CO_2R^6$, $-SR^{51}$ and $-OR^6$;

or phenyl optionally substituted by up to five groups $R^{21}$ which may be the same or different;

n represents zero or an integer from one to five;

$R^5$ and $R^6$, which may be the same or different, each represents a straight- or branched-chain alkyl group containing up to six carbon atoms which is optionally substituted by one or more halogen atoms;

$R^{51}$ represents a straight- or branched-chain alkyl group containing up to six carbon atoms which is optionally substituted by one or more halogen atoms;

X represents oxygen, $-(CR^9R^{10})_t-$ or $-N(R^{11})-$;

p represents zero, one or two; q represents zero, one or two;

m represents an integer from one to three;

$R^7$ and $R^8$, which may be the same or different, each represents:

the hydrogen atom; or a straight- or branched-chain alkyl group containing up to six carbon atoms optionally substituted by one or more halogen atoms;

$R^9$ and $R^{10}$, which may be the same or different, each represents:

the hydrogen atom;

a straight- or branched-chain alkyl or alkenyl group containing up to six carbon atoms which is optionally substituted by one or more halogen atoms; or phenyl optionally substituted by from one to five groups $R^{21}$ which may be the same or different;

t represents an integer from one to four; when t is greater than one the groups $-CR^9R^{10}-$ may be the same or different;

$R^{11}$ represents:

the hydrogen atom;

a straight- or branched-chain alkyl, alkenyl or alkynyl group containing up to ten carbon atoms which is optionally substituted by one or more halogen atoms; or phenyl optionally substituted from one to five groups $R^{21}$ which may be the same or different;

$R^{21}$ represents halogen, $R^6$, $-CO_2R^6$, $-COR^6$, $-OR^6$, nitro or cyano;

or an agriculturally acceptable salt or metal complex thereof.

2. A compound according to claim 1 characterised in that $R^1$ represents:

a straight- or branched-chain alkyl group containing up to six carbon atoms which is optionally substituted by one or more halogen atoms; or a cycloalkyl group containing from three to six carbon atoms optionally substituted by one or more methyl groups.

3. A compound according to claim 1 or 2 characterised in that $R^1$ represents a group selected from methyl, ethyl, isopropyl, 1-methylcyclopropyl and cyclopropyl.

4. A compound according to claim 1 or 2 characterised in that the phenyl ring is 2,4-disubstituted by two groups $R^2$; or is 2,3,4-trisubstituted by three groups $R^2$.

5. A compound according to claim 1 or 2 characterised in that:

$R^2$ represents:

a halogen atom;

a straight- or branched-chain alkyl, alkenyl or alkynyl group containing up to four carbon atoms optionally substituted by one or more halogen atoms;

a straight- or branched-chain alkyl group containing up to four carbon atoms which is substituted by a group $-OR^6$; or a group selected from $-COR^6$, $-CO_2R^6$, $-S(O)_pR^{51}$, $-X-S(O)_qR^{51}$, $-O(CH_2)_mOR^6$ and $-OR^6$;

X represents $-CH_2-$ or $-NR^{11}-$;

$R^6$ represents a straight- or branched-chain alkyl group containing up to four carbon atoms; and $R^{51}$ represents a straight- or branched-chain alkyl group containing up to four carbon atoms.

6. A compound according to claim 1 or 2 characterised in that:

$R^2$ represents:

a halogen atom;

a straight- or branched-chain alkyl group containing up to four carbon atoms optionally substituted by one or more halogen atoms;

a straight- or branched-chain alkyl group containing up to four carbon atoms which is substituted by a group $-OR^6$; or a group $-S(O)_pR^{51}$, wherein $R^{51}$ represents ethyl or methyl.

7. A compound according to claim 1 or 2 characterised in that $R^3$ represents the hydrogen atom or a straight- or branched-chain alkyl group containing up to four carbon atoms.

8. A compound according to any one of claim 1 or 2 characterised in that $R^4$ represents a straight- or branched-chain alkyl or alkenyl group containing up to six carbon atoms.

9. A compound according to claim 1 or 2 characterised in that $R^{11}$ represents the hydrogen atom or a straight- or branched-chain alkyl group containing up to six carbon atoms.

10. A compound according to claim 1 or 2 characterised in that n represents one, two or three.

11. A compound according to claim 1 characterised in that:

$R^1$ represents a cyclopropyl group;

$R^2$ represents a halogen atom or a group selected from trifluoromethyl, —S(O)$_p$R$^{51}$ and —X—S(O)$_q$R$^{51}$;

$R^3$ represents the hydrogen atom;

$R^4$ represents a straight- or branched-chain alkyl or alkenyl group containing from two to four carbon atoms;

n represents two or three;

$R^{51}$ represents methyl;

X represents —CH$_2$—;

p represents zero, one or two; and q represents zero, one or two.

12. A compound according to claim 1 which is:

3-cyclopropyl-2-(ethoxyiminomethyl)-1-(2-methylsulphonyl-4-trifluoromethylphenyl)propan-1,3-dione;

3-cyclopropyl-1-(2-methylsulphonyl-4-trifluoromethylphenyl)-2-(2-propenyloxyiminomethyl)propan-1,3-dione;

1-(4-chloro-2-methylsulphonylphenyl)-3-cyclopropyl-2-(ethoxyiminomethyl)propan-1,3-dione;

1-(2-chloro-4-methylsulphonylphenyl)-3-cyclopropyl-2-(ethoxyiminomethyl)propan-1,3-dione;

1-(4-chloro-3-fluoro-2-methylsulphenylphenyl)-3-cyclopropyl-2-(ethoxyiminomethyl)propan-1,3-dione;

3-cyclopropyl-1-(3,4-dichloro-2-methylsulphenylphenyl)-2-(ethoxyiminomethyl)propan-1,3-dione;

1-[4-bromo-2-(methylsulphenylmethyl)phenyl]-3-cyclopropyl-2-(ethoxyiminomethyl)propan-1,3-dione;

1-[4-bromo-2-(methylsulphinylmethyl)phenyl]-3-cyclopropyl-2-(ethoxyiminomethyl)propan-1,3-dione; or 1-[4-bromo-2-(methylsulphonylmethyl)phenyl]-3-cyclopropyl-2-(ethoxyiminomethyl)propan-1,3-dione;

or an agriculturally acceptable salt or metal complex thereof.

13. A herbicidal composition characterised in that it comprises as active ingredient a herbicidally effective amount of an oxime derivative of formula (I) as defined in claim 1 or an agriculturally acceptable salt or metal complex thereof, in association with an agriculturally acceptable diluent or carrier and/or surface active agent.

14. A herbicidal composition according to claim 13 in the form of an aqueous suspension concentrate, a wettable powder, a water soluble or water dispersible powder, a liquid water soluble concentrate, a liquid emulsifiable suspension concentrate, a granule or an emulsifiable concentrate.

15. A method for controlling the growth of weeds at a locus characterised in that it comprises applying to the locus a herbicidally effective amount of an oxime derivative of formula (I) as defined in claim 1 or an agriculturally acceptable salt or metal complex thereof.

16. A process for the preparation of an oxime derivative of formula (I) as defined in claim 1 characterised in that it comprises reacting a compound of formula II:

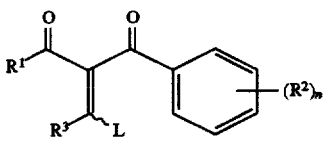

wherein $R^1$, $R^2$, $R^3$ and n are as defined in claim 1 and L is a leaving group, with a hydroxylamine of formula III:

$R^4O—NH_2$    III or a salt thereof, wherein $R^4$ is as defined in claim 1;

optionally followed by the conversion of the compound of formula (I) thus obtained into an agriculturally acceptable salt or metal complex thereof.

* * * * *